United States Patent

Koppenhoefer et al.

Patent Number: 5,288,911
Date of Patent: Feb. 22, 1994

[54] PREPARATION OF α,ω-AMINOALCOHOLS

[75] Inventors: Gerhard Koppenhoefer, Roemerberg; Wolfgang Schroeder, Bad Duerkheim; Dieter Voges, Mannheim, all of Fed. Rep. of Germany

[73] Assignee: BASF Aktiengesellschaft, Ludwigshafen, Fed. Rep. of Germany

[21] Appl. No.: 872,917

[22] Filed: Apr. 22, 1992

[30] Foreign Application Priority Data

Apr. 23, 1991 [DE] Fed. Rep. of Germany ....... 4113161

[51] Int. Cl.⁵ ............................................. C07C 209/16
[52] U.S. Cl. .................................... 564/480; 564/355; 564/402; 564/447; 564/453; 564/454; 564/474; 564/503; 564/508; 564/511
[58] Field of Search ............... 564/480, 474, 447, 402, 564/503, 511, 508, 355, 453, 454

[56] References Cited

U.S. PATENT DOCUMENTS

| | | | |
|---|---|---|---|
| 3,560,550 | 2/1971 | Griswold et al. | 558/310 |
| 3,652,545 | 3/1972 | Horlenko et al. | 540/609 |
| 4,151,204 | 4/1979 | Ichikawa et al. | 564/480 |

FOREIGN PATENT DOCUMENTS

| | | |
|---|---|---|
| 0021073 | 1/1981 | European Pat. Off. |
| 2180462 | 11/1973 | France |
| 1185310 | 3/1970 | United Kingdom |

Primary Examiner—Richard L. Raymond
Assistant Examiner—Scott C. Rand
Attorney, Agent, or Firm—John H. Shurtleff

[57] ABSTRACT

Preparation of α,ω-aminoalcohols of the general formula I $$HO-CH_2-X-CH_2-NH_2 \quad (I),$$

in which x denotes a $C_1$-$C_{20}$-alkylene chain optionally substituted by inert radicals and/or optionally interrupted by oxygen or nitrogen, by the reaction of α,ω-alkanediols of the general formula II $$HO-CH_2-X-CH_2-OH \quad (II),$$

in which the connecting member x has the meanings stated above, with ammonia and a catalyst at a temperature ranging from 150° to 300° C. and under a pressure of from 50 to 300 bar, wherein the catalyst used is one whose catalytically active material consists of iron to an extent of from 5 to 100% w/w.

7 Claims, No Drawings

PREPARATION OF α,ω-AMINOALCOHOLS

The present invention relates to a novel and improved process for the preparation of α,ω-aminoalcohols by the reaction of α,ω-alkanediols and ammonia at elevated temperature and pressure in the presence of a catalyst whose catalytically active material consists of iron to an extent of from 5 to 100% w/w.

α,ω-Aminoalcohols are intermediates having a variety of applications. Their versatility is a result of the fact that the molecule contains two different reactive terminal groups. Hitherto, there has been the drawback that only the simplest representative of this class of product (ethanolamine) can be synthesized in a simple manner, i.e., by ethoxylation of ammonia.

There has as yet been no way of economically manufacturing relatively long-chain, unbranched, aminoalcohols having terminal functional groups.

EP-A 21,073 describes the use of catalysts based on iron and cobalt for the preparation of amines from alcohols or carbonyl compounds. As is evident from the examples and the general description of the application of the catalyst, this reference concerns the replacement of an OH group in a molecule which contains in addition to this one OH group readily cleavable substituents of a different nature, e.g., a peralkylated amino group. The presence of hydrogen during the reaction is unnecessary.

U.S. Pat. No. 4,151,204 discloses the preparation of aminoalcohols using catalysts containing iron and cobalt. However, this describes the replacement of a readily replaceable secondary OH group by an $NH_2$ group, so that compounds are obtained, which contain, in addition to a primary OH group, a secondary $NH_2$ group in the molecule.

U.S. Pat. No. 3,652,545 discloses that the reaction of 1,6-hexanediol with ammonia produces, when carried out in contact with Raney-nickel or Raney-cobalt or a nickel-on-kieselguhr catalyst for the purpose of synthesizing N-(6-aminohexyl)hexamethyleneimine, 6-aminohexanol as one of the by-products. The said process is clearly neither designed nor suitable for the specific manufacture of this compound.

U.S. Pat. No. 3,560,550 discloses that 6-aminohexanol and related compounds can be intentionally obtained by passing a lactone together with ammonia, at from 250° to 300° C., as a gas over active $\gamma$-$Al_2O_3$ followed by hydrogenation of the resulting ω-hydroxynitrile over Raney-nickel to form the aminoalcohol. This is thus a multistage, i.e., non-straightforward and therefore uneconomical process.

GB-A 1,185,310 discloses that 6-aminohexanol can be obtained by reacting ε-caprolactam with ammonia at from 220° to 350° C. in an autoclave in contact with a ruthenium catalyst for a number of hours. Aminohexanol is formed as a by-product. This process cannot be developed to form an economical process for the production of this compound.

Some of the drawbacks of such routes reside in their complexity, in the use of expensively produced starting materials, and in the usually very poor yields obtained.

Thus it is an object of the present invention to overcome the aforementioned drawbacks.

Accordingly, we have found a novel and improved process for the preparation of α,ω-aminoalcohols of the general formula I $$HO-CH_2-X-CH_2-NH_2 \qquad (I),$$

in which X denotes a $C_1$-$C_{20}$-alkylene chain optionally substituted by inert radicals and/or optionally interrupted by oxygen or nitrogen,
by the reaction of α,ω-alkanediols of the general formula II $$HO-CH_2-X-CH_2-OH \qquad (II),$$

in which the connecting member X has the aforementioned meanings, with ammonia and a catalyst at a temperature ranging from 150° to 300° C. and under a pressure of from 50 to 300 bar, wherein the catalyst used in one whose catalytically active material consists of iron to an extent of from 5 to 100% w/w.

The process of the invention may be carried out as follows:

The α,ω-alkanediols of formula II, optionally in an inert solvent, and ammonia are fed in the presence of a catalyst under a pressure ranging from 50 to 300 bar and preferably from 150 to 250 bar and at a temperature of from 150° to 300° C. and preferably from 180° to 270° C., at a rate of from 0.1 to 2 l of α,ω-alkanediol of formula II per liter of catalyst per hour and preferably of from 0.2 to 1 l per liter per hour. Ammonia and the α,ω-alkanediol of formula II are used in a molar ratio of from 1:1 to 300:1 and preferably of from 1.5:1 to 100:1, and more preferably of from 2:1 to 20:1. The ammonia may be used in gaseous or, preferably, liquid form.

The reaction is controlled, for example, in such a manner that from about 50 to 70% of the α,ω-alkanediol is converted. The effluent is cooled, for example by pressure reduction, and the ammonia is separated, reliquefied if necessary, and recycled to the reaction if desired. The reaction mixture may be fractionated by distillation. The α,ω-aminoalcohols of formula I are obtained in purities of, for example, better than 98%. The unconverted diol of formula II may be recycled to the reaction. By-products may form which constitute desirable products, such as cyclic imines (morpholine, pyrrolidine, piperidine), or diamines (hexamethylenediamine).

Control of the reaction to give the desired conversion rates is preferably effected via the reaction temperature. As a general rule, the diol conversion declines as the temperature is decreased, but selectivity for the aminoalcohol increases. This generally has a value between 60 and 80%. Higher selectivities than 80% are possible but undesirable because the costs increase on account of the poorer conversion rate. With rising temperature the conversion of diol can be increased, but costs increase due to the poorer selectivity achieved, since an increasing portion of the diol reacts to the theoretically utilizable but in practice undesirable by-products.

The α,ω-alkanediols of formula II may be fed to the reactor either as pure substance or in the form of a solution. It is preferred to operate without additional solvent, although it may be advantageous on occasion to use a solution. This is especially the case when the diol of formula II has a high melting point. Examples of suitable solvents are cyclic ethers, such as tetrahydrofuran, and particularly tertiary amines, such as N-methyl morpholine.

Suitable reactors are preferably fixed-bed reactors, through which the reaction mixture passes either upwardly or, preferably, downwardly. The catalyst may be present therein in the form of a loose bed and consists of arbitrarily shaped particles.

Preference is given to pellets of which the major dimensions range from 4 to 8 mm, or extrudates of similar format. Suitable catalysts for the process of the invention are those whose catalytically active material consists of from 5 to 100% of iron and preferably of from 5 to 60% w/w of iron and from 0 to 95% w/w of cobalt.

The catalysts advantageously contain approximately equal weights of iron and cobalt; a content of at least 25% of cobalt should usually form the lower limit. Adding less than 5% of iron is usually equally unfavorable, as such catalysts hardly differ from pure cobalt catalysts. Cobalt catalysts in which from about 25 to 50% of cobalt are replaced by iron, are particularly efficacious in all respects.

One suitable method of obtaining iron/cobalt catalysts comprises the concurrent precipitation from a solution of iron and cobalt salts in the form of hydroxides or basic carbonates followed by treatment of the (heated) precipitate with reducing agents. The precipitation should be effected in dilute to moderately concentrated solution in order to obtain uniform precipitations. Approximately 0.1M to 1M solutions of the nitrates of iron(III) and cobalt(III) are particularly suitable. The sulfates and the chlorides may also be used if desired.

Precipitation is initiated by the use of soda or potash solution, which may have a strength of, for example, from 5 to 30%, at from about 60° to 90° C. the precipitation should continue through a period of from about 1 to 5 h, depending on the type of apparatus used. The pH is adjusted to about 7 and the precipitation is carried out, when using a batch method, by stirring the metal salt solution into excess alkali metal carbonate solution, so that throughout precipitation the precipitate is constantly surrounded by an excess of carbonate ions and the final pH is not below 7. In a continuous manufacturing method, the two solutions can be concurrently fed to the same stirred vessel, the rates of flow being adjusted such that the pH of the mixture is 7 or higher, i.e., the mixture is started with an excess of alkali carbonate and this is then maintained.

The above measures play a decisive role in the production of a good, in particular compression-resistant (i.e., durable) and nevertheless voluminous (i.e., porous and thus highly active) catalyst; in fact it is known per se to produce iron/cobalt catalysts by precipitating salt solutions thereof with, e.g., potash solution (cf. J. Am. Chem. Soc., 76, pp 319–323(1954)). It is also known to use iron/cobalt catalysts, produced via various routes, for hydrogenating amination, e.g., for the preparation of hexamethylenediamine or ethylenediamine. The disclosed production methods (cf. GB-PS 1,206,659, FR-PS 2,180,462 und U.S. Pat. No. 3,840,479), however, virtually always yield catalysts which are not sufficiently porous, so that their use in a fixed bed, e.g. in a tubular reactor, is only feasible using supporting material (GB-PS 1,206,659) or uneconomically large amounts of catalyst.

The precipitate is washed in the usual manner and dried, e.g., at from 100° to 150° C. It suffers a loss on ignition of from about 22 to 25% and contains inter alia from about 0.25 to 0.5% of alkali (sodium; as $Na_2O$). X-ray spectrographic analysis shows that it constitutes a mixture of cobalt carbonate ($CoCO_3$) and, predominantly, a compound of both metals having the structure of natural manasseite; similar artificially produced compounds have been described in, for example, DE-PS 2,024,282. Compounds containing exclusively or substantially only cobalt and iron are not, however, mentioned in said reference.

The proportion of said compound in the mixture containing cobalt carbonate probably depends on the ratio of the metals involved.

The particulate material obtained on heating to 300° C. or more is virtually amorphous radiographically. It can be worked to a paste with a little liquid (water or the like), kneaded and fabricated to shaped articles, such as are usual for catalysts, e.g., extrudates or pellets. The use of the unprocessed powder as a suspended catalyst is also possible. It is reduced with hydrogen prior to use in the usual manner. Another possibility is to carry out precipitation and processing in the presence of a chemically indifferent support, resulting in a cobalt/iron catalyst exhibiting, for example, a particularly large surface area.

The connecting member x in the compounds I and II has the following meanings:

X a $C_1$–$C_{20}$-alkylene chain such as —$(CH_2)$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, and —$(CH_2)_{20}$— and preferably $(CH_2)_2$ to $(CH_2)_{10}$, and more preferably $(CH_2)_3$ and $(CH_2)_4$.

a $C_1$–$C_{20}$-alkylene chain interrupted by oxygen or nitrogen, such as $CH_2$—O—$CH_2$ or

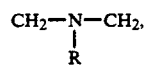

where R stands for hydrogen or methyl ($CH_3$), a $C_1$–$C_{20}$-alkylene chain substituted by inert radicals and preferably a $C_1$–$C_{20}$-alkylene chain substituted by from one to five inert radicals, and more preferably a $C_1$–$C_{20}$-alkylene chain substituted by from one to three inert radicals, a $C_1$–$C_{20}$-alkylene chain substituted by inert radicals and interrupted by oxygen or nitrogen and preferably a $C_1$–$C_{20}$-alkylene chain substituted by from one to five inert radicals and interrupted by oxygen or nitrogen, and more preferably a $C_1$–$C_{20}$-alkylene chain substituted by from one to three inert radicals and interrupted by oxygen or nitrogen.

Examples of suitable inert radicals are:

$C_1$–$C_8$-alkyl such as methyl, ethyl, n-propyl, isopropyl, n-butyl, isobutyl, sec-butyl, tert-butyl, n-pentyl, isopentyl, tert-amyl, n-hexyl, isohexyl, n-heptyl, isoheptyl, n-octyl and isooctyl and preferably $C_1$–$C_4$-alkyl such as methyl, ethyl, n-propyl, isopropyl, n-butyl, isobutyl, sec-butyl, and tert-butyl, and more preferably methyl and ethyl, $C_3$–$C_8$-cycloalkyl such as cyclopropyl, cyclobutyl, cyclopentyl, cyclohexyl, cycloheptyl and cyclooctyl and preferably cyclopentyl, cyclohexyl and cyclooctyl, aryl such as phenyl, 1-naphthyl, 2-naphthyl, 1-anthryl, 2-anthryl, and 9-anthryl and preferably phenyl, 1-naphthyl, and 2-naphthyl, and more preferably phenyl.

Suitable α,ω-aminoalcohols of the general formula I and their α,ω-alkanediols of the general formula II are, e.g.:

| α,ω-Aminoalcohol of formula I | α,ω-Alkanediol of formula II |
| --- | --- |
| 1-aminopropanol | propanediol |
| 1-aminobutanol | butanediol |
| 1-aminopentanol | pentanediol |
| 1-aminohexanol | hexanediol |
| 1-aminooctanol | octanediol |
| and more preferably | |
| 1-aminobutanol | 1,4-butanediol |
| 1-aminopentanol | 1,5-pentanediol |
| 1-aminohexanol | 1,6-hexanediol |

The aminoalcohols of the general formula I which can be produced by the process of the invention are intermediates for the preparation of pharmaceuticals (cf. U.S. Pat. No. 4,151,204) and also potentially for the preparation of thixotropic agents, dyes and anti-corrosive agents.

EXAMPLES

Manufacture of the catalyst

A catalyst having a relatively low bulk density is prepared by the following special process; its target composition is, say, 51.22% of $Fe_2O_3$ and 48.78% of $Co_3O_4$ (50% w/w of Fe to 50% w/w of Co):

60 kg of 20% strength soda solution are placed in a stirred vessel, heated to approximately 70° C. and, with stirring at constant temperature, a mixture of 33 kg of commercial iron nitrate solution having a content of 10.86% of $Fe_2O_3$ and 25.72 kg of cobalt nitrate solution having a content of 16.48% of $Co_3O_4$ is added over a period of 4 h, until the pH adjusts to 7.0, as measured with a glass electrode. The remaining amount of nitrate solution is then gradually added via feed-regulating means, whilst keeping the pH at 7.0. The resulting precipitate is isolated by filtration, washed with deionized water and dried at 120° C.

The precipitate still contains 0.47% of $Na_2O$ with a loss on ignition of 23%; X-ray spectographic analysis shows that it consists of a mixture of a small portion of $CoCO_3$ (moderately crystalline) and a very large portion of a manasseite-like structure (fine crystalline).

The precipitate is then decomposed at 350° C. in air. Most of the chemically combined volatile ingredients are liberated between 145° and 200° C. (maximum at 174° C.) and between 220° and 265° C. (maximum at 253° C.). There is obtained a powder having a bulk density of 458 g/l and a loss on ignition at 900° C. of 4.4%. It is kneaded with the addition of 2% of dilute nitric acid and sufficient water, extruded, dried and tempered at 400° C. Extrudates are obtained weighing 900 g/l and having a porosity of 0.42 cm³/g and a scratch hardness of 2.5 kg. The extrudates can be completely reduced in the temperature range 265° to 365° C. (maximum at 336° C.) under a blanket of hydrogen, in a slightly exothermic reaction. Following reduction, there is obtained, as shown by X-ray spectographic analysis, a cubi body-centered mixed crystal containing Fe and Co.

A catalyst produced in the above manner is suitable not only for the amination of saturated aminoalcohols, but also for the hydrogenation of nitriles and for simultaneous hydrogenation and amination of aminoalkenols and aminoalkynols. It is thus capable of hydrogenating C—N multiple bonds, C—C double bonds and C—C triple bonds.

EXAMPLE 1

The reactor contained 2.5 l of the catalyst described above containing 50% of iron and 50% of cobalt. It was reduced over a period of 2 d with hydrogen, the temperature being raised from 200° to 300° C.

The temperature in the reactor was set to 230° C. and the catalyst wetted with ammonia. There were then passed, per hour, 1.7 l of pentanediol (95% strength) and 5 l of ammonia (calculated as liquid) downwardly through the reactor. A pressure of 200 bar was maintained with hydrogen, and 200 l (S.T.P.) of hydrogen were withdrawn as off-gas per hour. In a long-duration test lasting several weeks, the effluent had an average composition (calculated free from ammonia and water) as follows:

| pentanolamine | 43% w/w |
| --- | --- |
| piperidine | 14% w/w |
| diaminopentane | 2% w/w |
| unconverted pentanediol | 34% w/w |
| other by-products | 7% w/w |

The content of by-products is approximately the same as the content of the impurities in the pentanediol used. The selectivity was 65%.

EXAMPLE 2

In a manner similar to that described in Example 1, a 50% strength solution of hexanediol in N-methyl morpholine was passed through the reactor at a rate of 2.5 l of solution per hour.

In a long-duration test lasting several weeks the effluent (calculated free from ammonia, water and N-methylmorpholine) had the following average composition:

| hexanolamine | 43% w/w |
| --- | --- |
| hexamethyleneimine | 5% w/w |
| hexamethylenediamine | 13% w/w |
| unconverted hexanediol | 36% w/w |
| other by-products | 3% w/w |

The selectivity was 68%.

EXAMPLE 3a

In a manner similar to that described in Example 1 there were passed, per hour, 0.75 l of diethylene glycol and 2.2 l of ammonia at 240° C. through the reactor and the pressure in the reactor was maintained using nitrogen instead of hydrogen.

The average composition of the effluent (calculated free from ammonia and water) was as follows:

| aminodiglycol | 28% w/w |
| --- | --- |
| morpholine | 2% w/w |
| unconverted diglycol | 62% w/w |
| by-products | 8% w/w |

The selectivity was 74%.

EXAMPLE 3b

Example 3a was repeated except that the pressure in the reactor was maintained using hydrogen.

The average composition of the effluent (calculated free from ammonia and water) was as follows:

| | |
|---|---|
| aminodiglycol | 44% w/w |
| morpholine | 18% w/w |
| unconverted diglycol | 32% w/w |
| by-products | 6% w/w |

The selectivity was 65%.

Comparative examples using other catalysts a) In a manner similar to that described in Example 1, a catalyst having the following composition was used as packing and it was reduced under the conditions stated:

| Feed | 66% of CoO<br>20% of CuO<br>7% of $Mn_3O_4$<br>4% of $MoO_3$<br>3% of $H_3PO_4$<br>0.75 l/h of diethylene glycol<br>2.2 l/h of $NH_3$ | | |
|---|---|---|---|
| Temperature | 150, 170, 190° C. | | |
| Pressure | 250 bar of $H_2$ | | |
| Composition of the effluent: | | | |
| | 150° C. | 170° C. | 190° C. |
| aminodiglycol | 13 | 17 | 20% w/w |
| morpholine | 7 | 10 | 34% w/w |
| unconverted diglycol | 71 | 67 | 4% w/w |
| by-products | 9 | 6 | 42% w/w |
| selectivity | 45 | 51 | 20% w/w |
| conversion | 29 | 33 | 96% w/w | b) In a manner similar to that described in Example 1, a catalyst having the following composition was used as packing and was reduced under the conditions stated:

| Feed | 46.5% of NiO<br>16.5% of CuO<br>30.0% of $Al_2O_3$<br>1.4% of $MoO_3$<br>0.75 l/h of diethylene glycol<br>2.2 l/h of $NH_3$ | |
|---|---|---|
| Temperature | 150° and 180° C. | |
| Pressure | 200 bar of $H_2$ | |
| Composition of the effluent: | | |
| | 170° C. | 190° C. |
| aminodiglycol | 16 | 26% w/w |
| morpholine | 8 | 29% w/w |
| unconverted diglycol | 72 | 28% w/w |
| by-products | 4 | 18% w/w |
| selectivity | 57 | 20% |
| conversion | 28 | 72% | c) In a manner similar to that described in Example 1, a catalyst having the following composition was used as packing and was reduced under the conditions stated:

| Feed | 4% of CuO<br>10% of CoO<br>10% of NiO<br>on $Al_2O_3$<br>0.75 l/h of hexanediol<br>2.2 l/h of $NH_3$ | | |
|---|---|---|---|
| Temperature | 160, 170, 180° C. | | |
| Pressure | 250 bar of $H_2$ | | |
| | 160° C. | 170° C. | 180° C. |
| hexanolamine | 13 | 20 | 21% w/w |
| hexamethylenimine | 1 | 2 | 5% w/w |
| hexamethylenediamine | 2 | 4 | 6% w/w |
| unconverted hexanediol | 84 | 70 | 62% w/w |
| other by-products | — | 4 | 6% w/w |
| selectivity | 79 | 66 | 55% w/w |
| conversion | 16 | 30 | 38% w/w | d) In a manner similar to that described in Example 1, a catalyst of the following composition was used as packing and reduced under the conditions stated:

| Feed | 23% of CoO<br>1% of $Mn_3O_4$<br>0.5% of $H_3PO_4$<br>0.2% of $Na_2O$<br>on $Al_2O_3$<br>0.75 l/h of pentanediol<br>2.2 l/h of $NH_3$ | | |
|---|---|---|---|
| Temperature | 160, 170, 180° C. | | |
| Pressure | 250 bar of $H_2$ | | |
| | 160° C. | 170° C. | 180° C. |
| pentanolamine | 11 | 14 | 16% w/w |
| piperidine | 4 | 5 | 7% w/w |
| unconverted pentanediol | 79 | 72 | 58% w/w |
| diaminopentane | — | — | — |
| other by-products | 6 | 9 | 20% w/w |
| selectivity | 51 | 49 | 36% |
| conversion | 21 | 28 | 42% |

The comparative examples a) to d) show qualitatively the same results as Examples 1 to 3, for example with regard to the influence of temperature on the selectivity. However, their quantitative differences are considerable: for a given temperature the selectivity is considerably lower than when using catalysts based on iron. The advantage of admixing cobalt to iron is shown by Example 5 below.

EXAMPLE 5

In a manner similar to that described in Example 1 there were passed, per hour, 0.37 l of pentanediol and 1.2 l of ammonia (liquid) to the reactor. The catalyst used was one consisting almost entirely of iron and containing no cobalt (similar to EP-A 101,584).

| Catalyst composition prior to reduction: | |
|---|---|
| iron | 93.30% w/w |
| alkali (K + Na) | 0.03% w/w |
| manganese | 0.09% w/w |
| graphite | 2.40% w/w |
| oxygen | 4.80% w/w |
| Composition of the effluent: | |
| | 240° C. | 250° C. |
| pentanolamine | 32 | 34% |
| piperidine | 5 | 9% |
| pentanediol | 58 | 52% |
| diaminopentane | — | — |
| others | 5 | 5% |
| selectivity | 75 | 71% |
| conversion | 42 | 48% |

We claim:

1. In a process for the preparation of $\alpha,\omega$-aminoalcohols of the formula I $$HO-CH_2-X-CH_2-NH_2 \quad (I),$$

in which X denotes a $C_1-C_{20}$-alkylene chain optionally substituted by inert radicals and/or optionally interrupted by oxygen or nitrogen, by the reaction of α,ω-alkanediols of the formula II $$HO-CH_2-X-CH_2-OH \qquad (II),$$

in which the connecting member X has the meanings stated above, with ammonia and a catalyst at a temperature ranging from 150° to 300° C. and under a pressure of from 50 to 300 bar, the improvement which comprises:

carrying out the reaction by continuously passing the reaction mixture through a fixed-bed catalyst in which the catalytically active material consists of iron to an extent of from 5 to 100% w/w and of cobalt to an extent of 0 to 95% w/w.

2. A process for the preparation of α,ω-aminoalcohols as claimed in claim 1, wherein the catalyst used is one whose catalytically active material consists of iron to an extent of from 5 to 60% w/w and of cobalt to an extent of from 40 to 95% w/w.

3. A process for the preparation of α,ω-aminoalcohols as claimed in claim 1, wherein the reaction is carried out in the presence of hydrogen and/or nitrogen.

4. A process as claimed in claim 1, wherein the reaction mixture is passed continuously through said fixed-bed catalyst at a rate of from 0.1 to 2 l of α,ω-alkanediol II per liter of catalyst per hour.

5. A process as claimed in claim 4, wherein the reaction mixture is passed downwardly through said fixed-bed catalyst.

6. A process as claimed in claim 4, wherein the rate of feed through said fixed-bed catalyst and the reaction temperature are controlled to maintain the selectivity for the aminoalcohol product I between about 60 and 80%.

7. A process as claimed in claim 6, wherein any unconverted diol II is recycled to the reaction.

* * * * *